(12) United States Patent
Vasseur et al.

(10) Patent No.: US 9,939,603 B2
(45) Date of Patent: Apr. 10, 2018

(54) BRAKE SYSTEM

(71) Applicant: NOVARTIS AG, Basel (CH)

(72) Inventors: Carlos Vasseur, Lake Forest, CA (US); Francisco Javier Ochoa, Cudahy, CA (US); Timm Redder, Ladera Ranch, CA (US)

(73) Assignee: Novartis AG (CH)

( * ) Notice: Subject to any disclaimer, the term of this patent is extended or adjusted under 35 U.S.C. 154(b) by 98 days.

(21) Appl. No.: 15/047,127

(22) Filed: Feb. 18, 2016

(65) Prior Publication Data

US 2017/0082819 A1    Mar. 23, 2017

Related U.S. Application Data

(60) Provisional application No. 62/222,038, filed on Sep. 22, 2015.

(51) Int. Cl.
| | |
|---|---|
| *A61B 3/14* | (2006.01) |
| *G02B 21/00* | (2006.01) |
| *G02B 7/00* | (2006.01) |
| *F16D 63/00* | (2006.01) |
| *A61B 3/13* | (2006.01) |
| *G02B 21/24* | (2006.01) |
| *G02B 21/36* | (2006.01) |
| *F16M 11/04* | (2006.01) |
| *F16M 11/18* | (2006.01) |

(Continued)

(52) U.S. Cl.
CPC .............. *G02B 7/001* (2013.01); *A61B 3/13* (2013.01); *A61B 3/132* (2013.01); *A61B 3/152* (2013.01); *F16D 63/002* (2013.01); *F16M 11/04* (2013.01); *F16M 11/18* (2013.01); *G02B 21/0012* (2013.01); *G02B 21/24* (2013.01); *G02B 21/368* (2013.01); *A61B 2090/506* (2016.02); *A61B 2090/508* (2016.02)

(58) Field of Classification Search
CPC .......... G02B 7/001; A61B 3/13; A61B 3/132; A61B 3/152; F16D 63/002; H02K 7/10; H02K 7/11; H02K 7/1021–7/1026
USPC ............. 310/76, 103–110; 351/205; 359/384
See application file for complete search history.

(56) References Cited

U.S. PATENT DOCUMENTS

| | | | |
|---|---|---|---|
| 5,098,426 A * | 3/1992 | Sklar ...................... | A61F 9/008 219/121.6 |
| 5,825,536 A | 10/1998 | Yasunaga et al. | |

(Continued)

*Primary Examiner* — Stephone B Allen
*Assistant Examiner* — Travis Fissel

(57) ABSTRACT

An ophthalmic surgical apparatus may include a tower extending upward from a support base, and a user-positionable arm extending from the tower to support an optical instrument attached to a distal end of the user-positionable arm. The user-positionable arm may include four members that are pivotably connected to each other. An electromagnetic brake strut may be pivotably attached in a diagonal relationship to at least two of the four members. The electromagnetic brake strut may include a rotatable lead screw having first and second lead screw end regions and a nut attached to the first pivot joint. The first lead screw end region may be threadably received into the nut. An electromagnetic clutch allows lead screw rotation when an electrical voltage is applied thereto. The electromagnetic clutch may be attached to the second pivot joint and may include a bearing that supports the second lead screw end region.

22 Claims, 5 Drawing Sheets

(51) Int. Cl.
*A61B 3/15* (2006.01)
*A61B 90/50* (2016.01)

(56) References Cited

U.S. PATENT DOCUMENTS

| | | |
|---|---|---|
| 6,364,268 B1 | 4/2002 | Metelski |
| 2002/0108874 A1 | 8/2002 | Metelski |
| 2003/0117703 A1 | 6/2003 | Metelski |
| 2005/0155444 A1* | 7/2005 | Otaki .................... B60T 13/746 74/89 |
| 2005/0224664 A1* | 10/2005 | Metelski ............... F16F 9/0209 248/123.11 |
| 2008/0009989 A1* | 1/2008 | Kim ..................... B60N 2/0232 701/36 |
| 2014/0055850 A1* | 2/2014 | Doi .................... G02B 21/0012 359/384 |
| 2014/0213414 A1 | 7/2014 | Balandis et al. |

* cited by examiner

BRAKE SYSTEM

CROSS REFERENCE TO RELATED APPLICATIONS

This application claims the benefit of U.S. Provisional Application No. 62/222,038, filed Sep. 22, 2015, the contents being incorporated herein by reference.

BACKGROUND

Floor standing microscopes with user-positionable arms are used in many ophthalmic medical procedures, e.g. ophthalmic surgery. Conventional ophthalmic microscopes may utilize a hydraulic arm locking system that may become unreliable due to fluid leaks. Alternative arm locking systems may suffer from positioning backlash, noisy operation, or excessive friction during use. Accordingly, there is a need in the art for an ophthalmic surgical device (such as an ophthalmic microscope) that has a user-positionable arm with improved reliability, reduced backlash, or smoother or quieter operation.

SUMMARY

According to one aspect, the present disclosure describes an ophthalmic microscope that may include a support base, a tower extending upward from the support base; a user-positionable arm extending from the tower and having a supported end that is attached to the tower; and a microscope head attached to a distal end of the user-positionable arm. The user positionable arm may include a four member linkage and an electromagnetic brake strut. The electromagnetic brake strut may include a nut and an electromagnetic clutch. The four member linkage may include four members that are pivotably connected to each other. The electromagnetic brake strut may be pivotably attached in a diagonal relationship to at least two of the four members at a first strut pivot joint and at a second strut pivot joint. The electromagnetic brake strut may include a rotatable lead screw. The rotatable lead screw may include a first lead screw end region and a second lead screw end region. The nut may be attached to the first strut pivot joint. The first lead screw end region may be received into the nut. The electromagnetic clutch may be attached to the second strut pivot joint. The electromagnetic clutch may be operable to permit rotation of the rotatable lead screw relative to the electromagnetic clutch when an electrical voltage is applied to the electromagnetic clutch.

According to another aspect, an ophthalmic surgical apparatus may include a rolling base, a tower extending from the rolling base, a user-positionable arm extending from the tower and having a supported end that is attached to the tower, and an optical instrument attached to a distal end of the user-positionable arm. The user-positionable arm may include a four member linkage having four members that are pivotably connected to each other and an electromagnetic brake strut. The electromagnetic brake strut may be pivotably in a diagonal relationship to at least two of the four members at a first strut pivot joint and a second strut pivot joint. The electromagnetic brake strut may include a rotatable lead screw, a nut, and an electromagnetic clutch. The rotatable lead screw may include a first screw end region and a second lead screw end region. The nut may be attached to the first strut pivot joint. The first lead screw end region may be threaded into the nut. The electromagnetic clutch may allow rotation of the lead screw when an electrical voltage is applied to the electromagnetic clutch. The electromagnetic clutch may be attached to the second strut pivot joint.

The various aspects of the disclosure may include one or more of the following features. A first member and a second member of the four member linkage may be longer than a third member and a fourth member of the four member linkage. The first member and second member may be pivotably connected by the third member and the fourth member. The first member may be positioned above the second member. The third member may be coupled to the tower, and the fourth member may be coupled to the microscope head. The four member linkage may form a parallelogram shape with the first member and the second member being substantially parallel to each other. The electromagnetic brake strut may have a backdriving configuration. The electromagnetic brake strut may have a length in the range of 5 inches to 30 inches. The electromagnetic brake may form an angle with the second member. The angle may be in the range of 5 degrees to 15 degrees. The nut may be attached to the second member at the first strut pivot joint, and the electromagnetic clutch may be attached to the fourth member at the second strut pivot joint. A weight compensation strut may be pivotably attached to the first member and the second member. The weight compensation strut may include a compressed gas spring. The weight compensation strut may have a compressed length in the range of 10 inches to 30 inches. The weight compensation strut may form an angle with the first member. The angle may be in the range of 5 degrees to 15 degrees. Each of the first member and the second member may define an arm length in the range of 15 inches to 30 inches. Rotation of the rotatable lead screw may provide 15 inches to 30 inches of vertical travel of the microscope head. The support base may be a rolling support base that is supported from underneath by a plurality of rollers. The tower may define a vertical axis. The supported end of the user-positionable arm may be rotatably attached to the tower to allow rotation of the user-positionable arm relative to the tower about the vertical axis. A display screen may be electrically attached to the microscope head. The rotatable lead screw may be formed from stainless steel and may include external threads having a spiral lead in the range of 0.5 inches per turn to 2 inches per turn. The nut may have an internally threaded bore that is engaged with external threads of the rotatable lead screw. The rotatable lead screw may include an external spiral bearing race. The non-rotating nut may include a plurality of internal metal balls that roll partially within the external spiral bearing race. The electromagnetic clutch may include a bearing that supports the second lead screw end region. The electromagnetic brake strut may have a backdriving configuration.

It is to be understood that both the foregoing general description and the following drawings and detailed description are exemplary and explanatory in nature and are intended to provide an understanding of the present disclosure without limiting the scope of the present disclosure.

DETAILED DESCRIPTION

Figure 1:
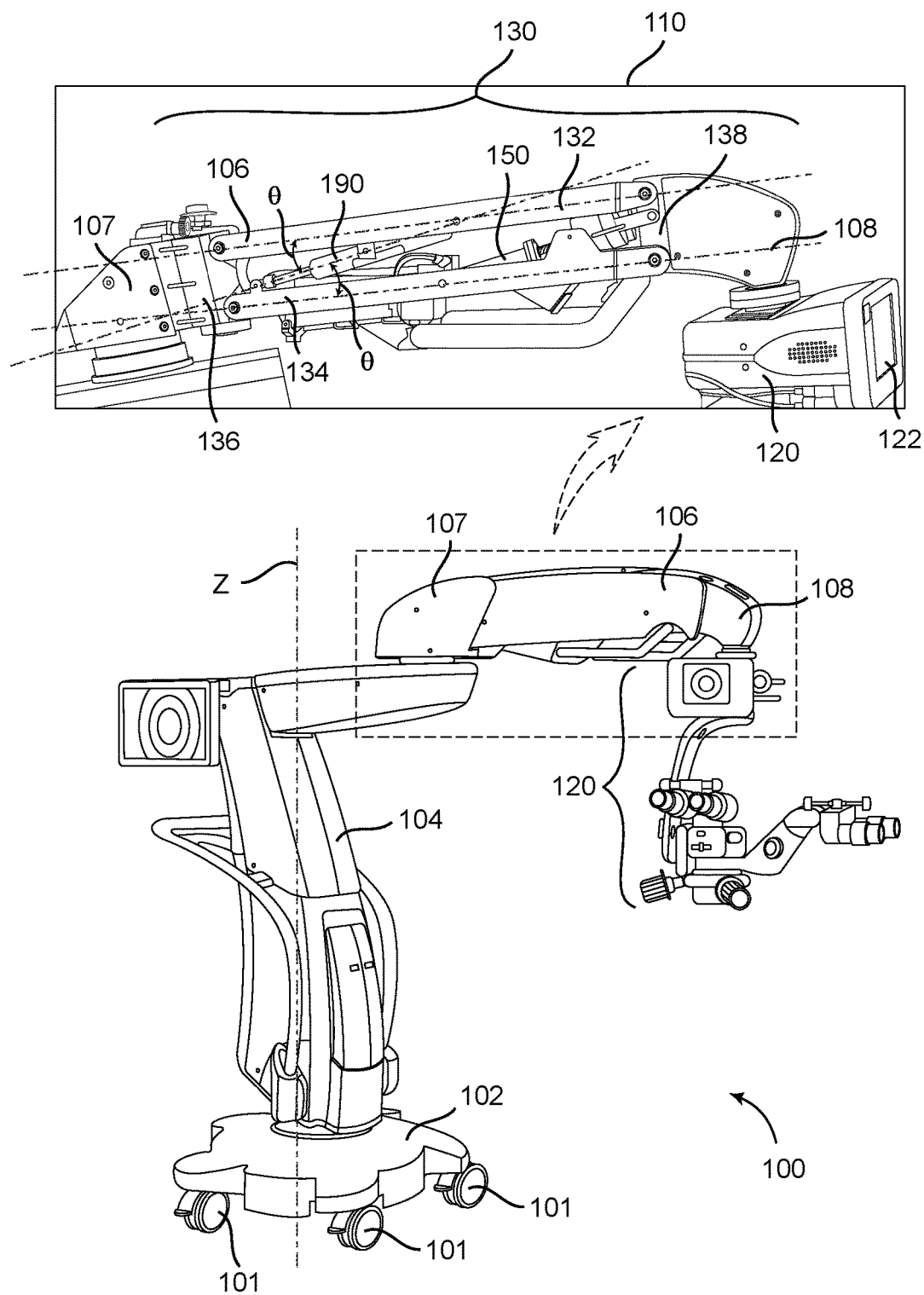
FIG. 1 depicts an example ophthalmic microscope.

FIG. 1 depicts an example ophthalmic microscope 100. As shown in FIG. 1, the example ophthalmic microscope 100 may include a support base 102 and a tower 104 extending upward from the support base 102. A user-positionable arm 106 may extend from the tower 104, with a supported end 107 that is attached to the tower 104. A microscope head 120 may be attached to a distal end 108 of the user-positionable arm 106.

The inset region 110 of FIG. 1 is an expanded view of the user-positionable arm 106, with an outer cover removed therefrom to reveal internal structural details. As can be seen in the inset region 110 of FIG. 1, the user-positionable arm 106 may include a four member linkage 130 having four members 132, 134, 136, 138 that are pivotably connected to each other. For example, in some instances, the members 132 and 134 may be elongated members and may be longer than members 136 and 138. The members 132, 134 may be pivotably connected by members 136 and 138.

In the example shown in FIG. 1, the support base 102 may optionally be a rolling support base that is supported from underneath by a plurality of rollers 101. The tower 104 may define a vertical axis Z, and the supported end 107 of the user-positionable arm 106 may be rotatably attached to the tower 104 to allow rotation of the user-positionable arm 106 relative to the tower 104 about the vertical axis Z. In some implementations, the ophthalmic microscope 100 may preferably include a display screen 122 that is electrically attached to the microscope head 120.

In some instances, the four member linkage 130 (shown in the inset region 110 of FIG. 1) optionally forms a parallelogram shape, with the members 132 and 134 being substantially parallel to each other. The member 132, as shown in FIG. 1, is positioned above the member 134. As shown in FIG. 1, the member 136 may be attached to the tower 104 at the proximal end 107 of the user-positionable arm 106. In some instances, the member 136 may be affixed to the tower 104 at the proximal end 107 of the user-positionable arm 106. The member 138 may be attached to the microscope head 120 at the distal end 108 of the user-positionable arm 106. In some instances, the member 138 may be affixed to the microscope head 120 at the distal end 108 of the user-positionable arm 106.

In the example shown in FIG. 1, an electromagnetic brake strut 150 may be pivotably attached in a diagonal relationship to at least two of the members 132, 134, 136, 138. For example, as shown in FIG. 1, the brake strut 150 is pivotably attached in a diagonal relationship with members 134 and 138. A weight compensation strut 190 (e.g., a compressed gas spring) may optionally be pivotably attached to the members 132, 134. In some instances, the weight compensation strut 190 may optionally have a compressed length in the range of 10 inches to 30 inches, and define an angle θ with the member 132 or the member 134 in the range of 5 degrees to 15 degrees (as shown in FIG. 1). In other implementations, a compressed length of the weight compensation strut 19 may be longer or shorter than the example range above. Additionally, in other implementations, the angle θ formed between the weight compensation strut 190 and one of the member 132 or the member 134 may be larger or smaller than the example range above.

Figure 2:
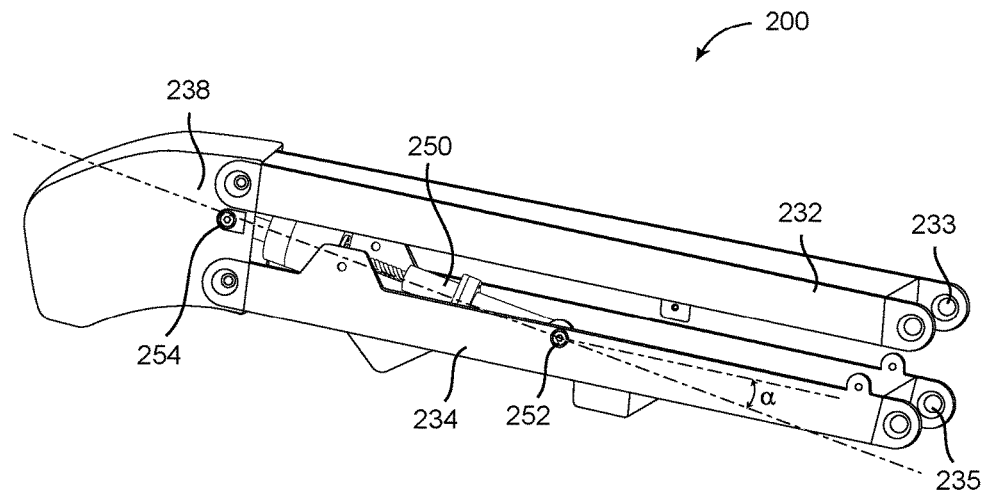
FIG. 2 depicts an example user-positionable arm mechanism for an ophthalmic surgical apparatus.

FIG. 2 depicts an example user-positionable arm mechanism 200 for an ophthalmic surgical apparatus. The user-positionable arm mechanism 200 of FIG. 2 includes three members 232, 234, and 238. In some instances, members 232 and 234 may be elongate members and may be longer than member 238. The member 238 may be disposed at a distal end of the user-positionable arm mechanism 200.

If the members 232 and 234 were pivotably attached to a supporting tower (such as, for example, the tower 104 shown in FIG. 1) at locations 233 and 235, respectively, then the user-positionable arm mechanism 200 would form a four member linkage. The member 238 may be attached to and support an optical instrument. In some instances, the member 238 may be affixed to and support an optical instrument. In the example of FIG. 2, an electromagnetic brake strut 250 is shown to be optionally pivotably attached in a diagonal relationship to the member 238 and the member 234, at first and second strut pivot joints 252, 254.

Figure 3:
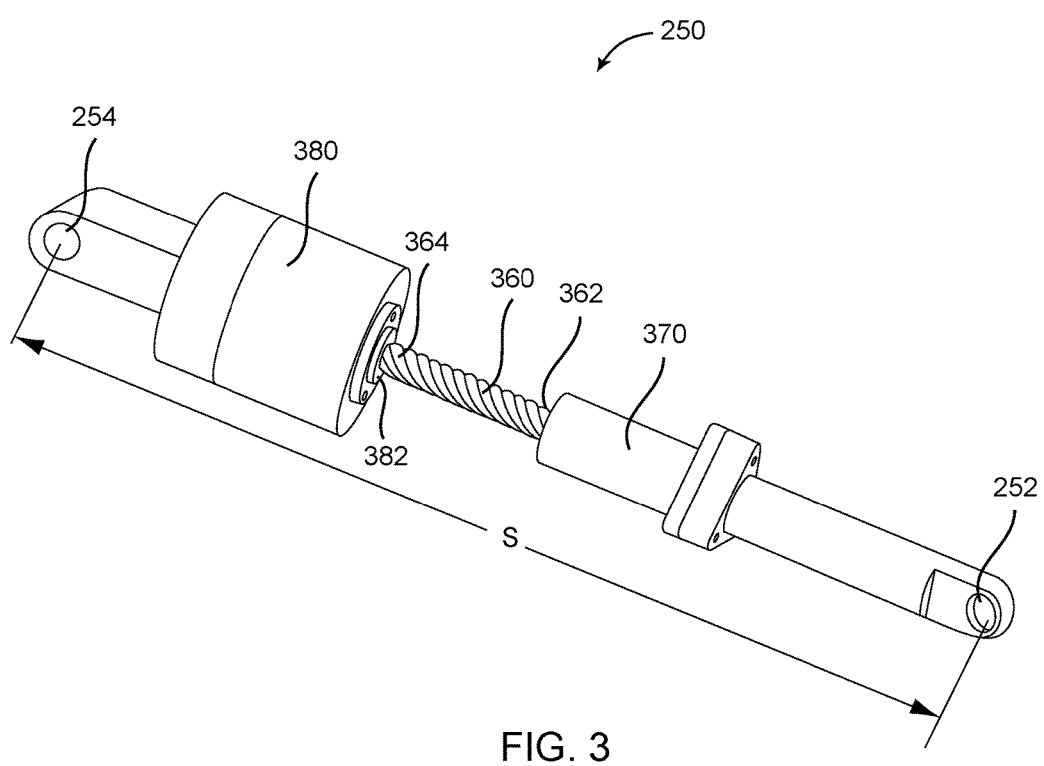
FIG. 3 depicts an example electromagnetic brake strut for use in a user-positionable arm.

FIG. 3 depicts an example electromagnetic brake strut 250 for use in a user-positionable arm. In the example of FIG. 3, the electromagnetic brake strut 250 may include a rotatable lead screw 360 having first and second lead screw end regions 362, 364. A nut 370 may be attached to the first strut pivot joint 252. In some instances, the nut 370 may be affixed to the first strut pivot joint 252. Thus, in some instances, the nut 370 may be non-rotatable relative to the first strut pivot joint 252. The first lead screw end region 362 may be threaded into nut 370. The electromagnetic brake strut 250 also includes an electromagnetic clutch 380. In some implementations, the electromagnetic clutch 380 may be a permanent magnet brake device. Moreover, the electromagnetic clutch 380 may be any device that is selectively operable to permit rotational movement of the lead screw 360 relative to the electromagnetic clutch 380 while maintaining the axial position of the lead screw 360 relative thereto.

The lead screw 360 is coupled to the electromagnetic clutch 380 and is operable to selectively rotate relative thereto. In a de-energized state, the lead screw 360 is prevented from rotating relative to the electromagnetic clutch 380. In an energized state, the lead screw 360 is permitted to rotate relative to the electromagnetic clutch 380. Also, a position of the lead screw 360 is axially fixed relative to the electromagnetic clutch 380 in both the de-energized state and the energized state. Thus, while the electromagnetic clutch 380 is in an energized state, the lead screw 360 is freely rotatable relative thereto but the axial position of the lead screw 360 relative to the electromagnetic clutch 380 remains fixed. In a de-energized state, both the rotational position and axial position of the lead screw 360 is fixed relative to the electromagnetic clutch 380.

In the example of FIG. 3, an electromagnetic clutch 380 allows rotation of the lead screw 360 only when a voltage is applied thereto. For example, the microscope head (e.g., the microscope head 120 of FIG. 1) may optionally include a switch, such as a normally-open momentary contact switch, that, when closed, applies the electrical voltage to the electromagnetic clutch 380.

In operation, a user may close a switch, such as a normally-open momentary contact switch, resulting in the application of a voltage to the electromagnetic clutch 380. As a result, the electromagnetic clutch 380 is energized. Referring to FIGS. 1 and 3, this switch may be provided on the user-positionable arm 106, on the microscope head 120 (or any device attached to the distal end 108 of the user positionable arm 106), or at any other location on the ophthalmic microscope 100. In still other implementations, the switch may be located remote from the ophthalmic microscope 100, such as on a remote control device. When the contact switch is closed and a voltage is applied to the electromagnetic clutch 380, the lead screw 360 is permitted to rotate relative to the electromagnetic clutch 380. A user may then manipulate the arm mechanism 200 in a vertical direction, for example. As arm mechanism 200 is moved vertically, the nut 370 causes the lead screw 360 to rotate relative thereto. This rotation causes the lead screw 360 to axially move relative to the nut 370. As a result, the length S of the brake strut 250 is changed.

When the arm mechanism 200 is at a desired position, the user may release the switch and de-energize the electromagnetic clutch 380. As a result, the electromagnetic clutch 380 locks the lead screw 360 relative thereto. Therefore, any subsequent attempt to vertically manipulate the arm mechanism 200 in the vertical direction does not result in movement of the arm mechanism 200. That is, the de-energized electromagnetic clutch 380 prevents the brake strut 250 from changing its length S and thereby prevents a change to the vertical position of the arm mechanism 200.

Although the brake strut 250 is connected to the example arm mechanism 200 in such a way as to control a vertical position of the arm mechanism 200, the scope of the disclosure is not so limited. Rather, a brake strut within the scope of the disclosure may be used to control a horizontal position of an arm mechanism, or, more generally, the brake strut may be incorporated so as to control movement in any desired direction. Further, multiple brake struts may be incorporated into an arm mechanism to control multiple directions of movement.

Referring again to FIG. 3, the electromagnetic clutch 380 may be attached to the second strut pivot joint 254. In some instances, the electromagnetic clutch 380 may be affixed to the second strut pivot joint 254. The electromagnetic clutch 380 may also include a bearing 382 that supports the second lead screw end region 364. In some implementations, the electromagnetic brake strut 250 may have a length S in the range of 5 inches to 30 inches between the first and second strut pivot joints 252, 254. However, the scope of the disclosure is not so limited. In other instances, the length S may be longer or shorter than the indicated range. Moreover, in other instances, the length S may be selected to be any desirable length.

As a result of the threaded connection between the lead screw 360 (e.g., at the first lead screw region 362) and the nut 370, rotation of the lead screw 360 relative to the nut 370 causes a distance S between the first strut pivot joint 252 and the second strut pivot joint 254 to change. For example, when the lead screw 360 is rotated in a first direction (such as when a user moves the arm mechanism in a second vertical direction), the first and second strut pivot point 252 and 254 are drawn towards each other, thereby reducing the distance S. When the lead screw 360 is rotated in a second direction, opposite the first direction, the first and second strut pivot point 252 and 254 are pushed apart from each other, thereby increasing the distance S. Thus, the electromagnetic clutch 380 may be operable to rotate the lead screw 360 relative to the nut 370 in opposing directions so as to lengthen or shorten the brake strut 250.

In some implementations, the lead screw 360 may be formed from stainless steel. Further, the lead screw 360 may include external threads that have a lead (i.e., the amount of axial travel per one 360° rotation of the lead screw 360) in the range of 0.5 inches per turn to 2 inches per turn. However, the scope of the disclosure is not so limited. In other instances, the lead of the threads of the lead screw 360 may be greater or less than 0.5 inches per turn to 2 inches per turn. Thus, the lead of the threads of the lead screw 360 may be any desired lead.

The nut 370 may have an internally threaded bore that is conventionally engaged with external threads of the lead screw 360. In some implementations, the nut 370 may include an internally lubricated polymeric material. For example, the nut 370 may include a polyoxymethylene polymer containing a polytetrafluoroethylene lubricant. In some implementations, the nut 370 may be fabricated from bronze and be lubricated with grease. In some instances, the nut 370 may be externally lubricated. In still other implementations, the lead screw 360 may include an external spiral bearing race, and the nut 370 may include a plurality of internal metal balls that roll partially within such external spiral bearing race.

The electromagnetic brake strut 250 may have a backdriving configuration. That is, with the electromagnetic clutch 380 energized and in an unlocked condition, when an axial pulling force or pressing force is applied at the strut pivot joints 252, 254, the lead screw 360 freely rotates relative to the nut 370. The relative rotation between the lead screw 360 and the nut 370 is a result of the interaction between the spiral bearing race of the lead screw 360 and the mating features of the nut 370 (e.g., a mating threaded surface, a plurality of metal balls, etc.). Therefore, with the electromagnetic clutch 380 energized, a user may freely reposition the arm mechanism 200 (e.g., extend or retract the brake strut 250) as a result of the backdriving configuration of the brake strut 250. Once the arm mechanism 200 is at a desired position, the electromagnetic clutch 380 may be de-energized, causing the electromagnetic clutch 380 to lock the brake strut 250 and the arm mechanism incorporating the brake strut 250, such as, for example, arm mechanisms 200, 400, 500, and 600, to be fixed at the desired position.

A backdriving configuration may accomplished by adjusting any number of characteristics of the brake strut 250. Example characteristics may include a pitch of the spiral bearing race of the rotatable lead screw 260 and mating feature of the nut 370; the material of the lead screw 360 and/or mating feature of the nut 370; surface finish of the lead screw 360 and/or mating feature of the nut 370; and the coefficient of friction between the lead screw 360 and the mating feature of the nut 370. Other characteristics of the brake strut 250 may also be applicable. For example, a surface treatment or lubricant applied to at least one of the lead screw 360 and the nut 370. Moreover, a plurality of different combinations of these characteristics and/or other characteristics of the brake strut 250 may be selected to produce a backdriving configuration.

Figure 7:
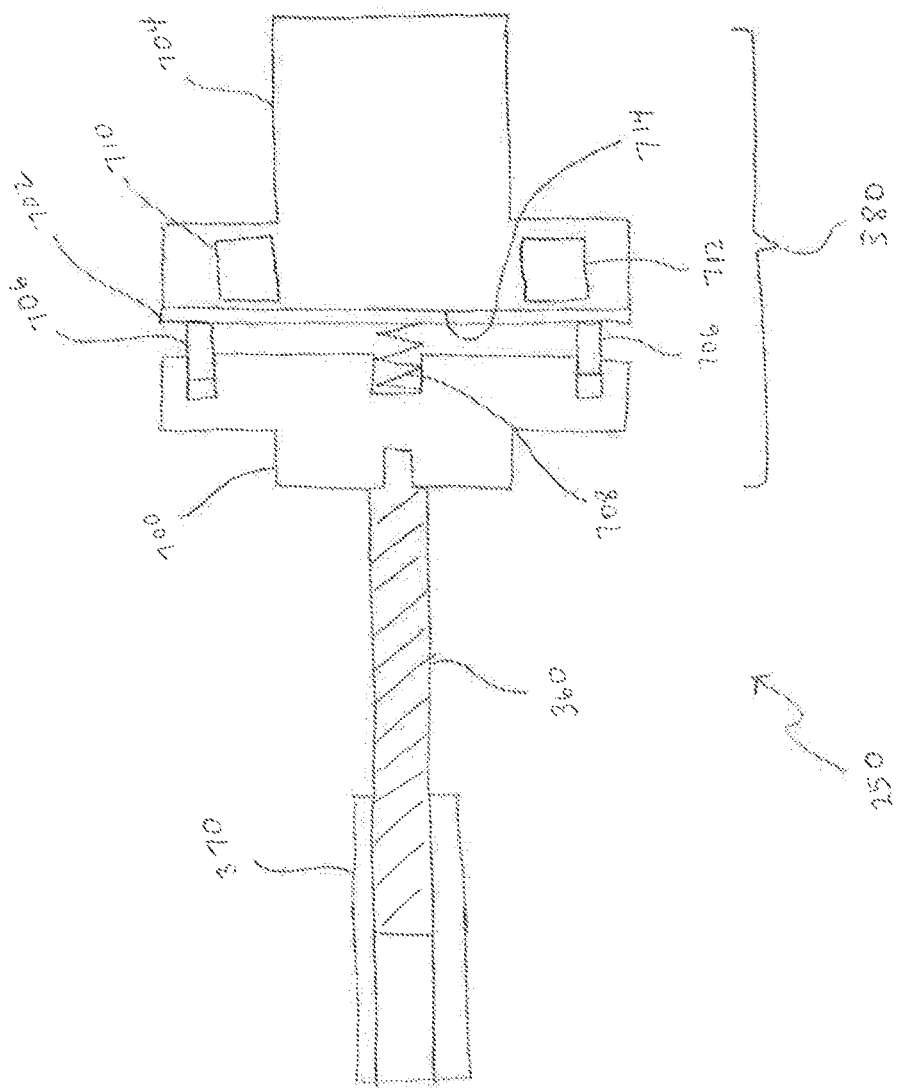
FIG. 7 shows a schematic view of an example electromagnetic brake strut.

FIG. 7 shows a schematic of an example implementation of the brake strut 250. FIG. 7 shows the nut 370 engaged with the lead screw 360. As explained above, the nut 370 and the lead screw 360 may be threadably engaged to each other such that rotation of the lead screw 360 relative to the nut 370 results in longitudinal displacement of the lead screw 360 relative to the nut 370.

FIG. 7 also shows that the electromagnetic clutch 380 includes a rotor 700, a friction plate 702, and a brake housing 704. The rotor 700 is coupled to the lead screw 360 such that the lead screw 360 and the rotor 700 rotate together. The friction plate 702 may include pins 706 that are slideably received into slots formed in the rotor 700. A spring 708 is coupled to the rotor 700 at a first end and to the friction plate 702 at a second end. By this construction, the friction plate 702 is permitted to be axially displaced from the rotor 700 while simultaneously rotatable with the rotor 700. Axial displacement of the friction plate 702 towards the brake housing 704 causes the spring 708 to expand, which produces a biasing force that urges the friction plate 702 back towards the rotor 700.

The brake housing 704 includes a magnet 710 and an electromagnet 712. Although FIG. 7 shows a single magnet 710 and a single electromagnet 712, other implementations may include two or more magnets 710 and/or electromagnets 712. In some implementations, the magnet 712 may be a rare-earth magnet. However, in other implementations, the magnet 712 may be any other type of magnet. The brake housing 704 may also include a frictional engaging surface 714 that is adapted to frictionally engage the friction plate 702 when the electromagnetic clutch 380 is de-energized.

For the example electromagnetic clutch 380 shown in FIG. 7, the electromagnetic clutch 380 is in an energized condition when the electromagnet 712 is energized, and the electromagnetic clutch 380 is an a de-energized condition when the electromagnet 712 is de-energized. The magnet 710 produces a magnetic force that attracts the friction plate 702. Thus, when the electromagnet 712 is de-energized, the magnet 710 displaces the friction plate 702 towards the brake housing 704 and into contact and frictional engagement with the frictional engaging surface 714, and the spring 708 is expanded. The frictional engagement between the friction plate 702 and the frictional engagement surface 714 resists rotation of the rotor 700 and lead screw 360 relative to the brake housing 704. As a result, the brake strut 250 is in a locked configuration.

When the electromagnet 712 is energized, the electromagnet 712 counteracts the magnetic force produced by the magnet 710. As a result, the biasing force produced by the spring 708 urges the friction plate 702 back towards the rotor 700, disengaging the friction plate 702 from the frictional engaging surface 714. With the friction plate 702 disengaged from the frictional engaging surface 714, the rotor 700 and lead screw 360 are free to rotate relative to the brake housing 704.

As a result of a backdriving configuration of the brake strut 250, when the electromagnetic clutch 380 in an energized condition, a user may extend or retract the brake strut 250 by applying an axial tensile or compression force thereto. For example, a user may extend the brake strut 250 by applying a pulling force to the strut pivot joints 252, 254 of the brake strut 250. Similarly, a user may shorten or retract the brake strut 250 by applying a pressing force to the strut pivot joints 252, 254 of the brake strut 250. Referring to FIG. 2, with the brake strut 250 in an energized condition, a user may apply a downward or upward vertical force to reposition the user-positionable arm mechanism 200. When the electromagnetic clutch 380 is de-energized, the brake strut 250 locks and the position of the arm mechanism 200 is fixed into the position selected by the user.

With a backdriving configuration, the brake strut 250 may be extended or retracted even when the electromagnetic clutch 380 is the de-energized or locked condition. In such cases, the brake strut 250 may be forcedly extended or retracted by simply applying sufficient force to extend or retract the brake strut 250. An axial force with a sufficient magnitude (e.g., a magnitude sufficient to overcome the normal force between the friction plate 700 and frictional engaging surface 714) can overcome the frictional force between the frictional engaging surface 714 and the friction plate 702, which results in rotation of the lead screw 360 and rotor 700 relative to the brake housing 704. This characteristic provides a safety feature should power be lost, for example, during a surgical procedure. Therefore, even with a loss of power, the brake strut 250 and, consequently, an arm mechanism incorporating the brake strut 250 may be made to move by applying a force sufficient to overcome the frictional force between the friction plate 702 and the frictional engaging surface 714.

Referring again to FIG. 2, the electromagnetic brake strut 250 may form an angle α with the member 234. In some instances, angle α may be in the range of 5 degrees to 15 degrees. In other implementations, the angle α may be larger or smaller than the example range. Thus, in some instances, the angle α may be any desirable angle. Still referring to FIGS. 2 and 3, the nut 370 may be attached to the member 234 via strut pivot joint 252, and the electromagnetic clutch 380 may be attached to the member 238 via the second strut pivot joint 254.

Figure 4:
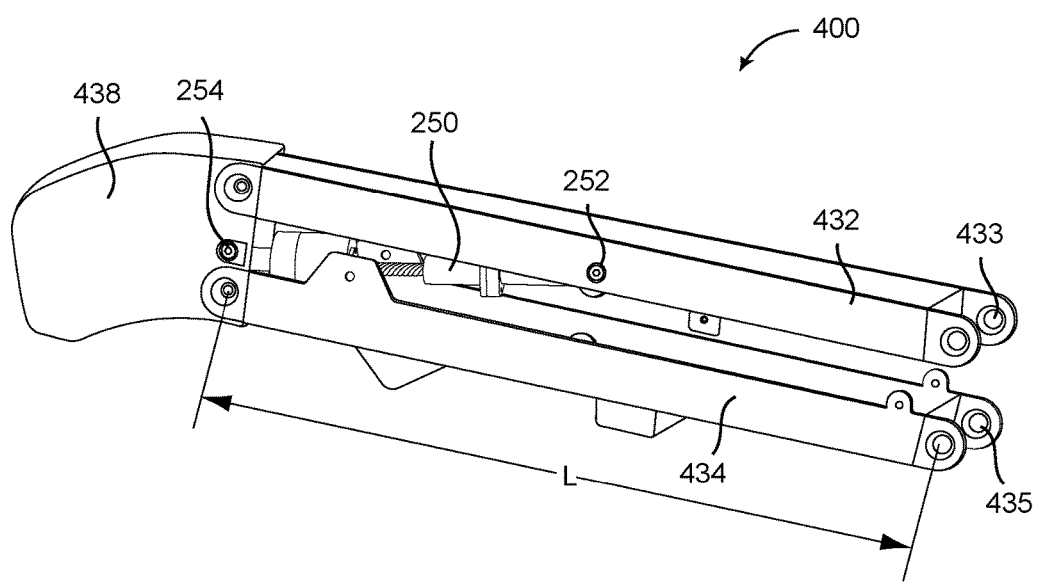
FIG. 4 depicts an example user-positionable arm mechanism for an ophthalmic surgical.

However, that example shown in FIGS. 2 and 3 is not the only configuration contemplated herein. For example, FIG. 4 depicts another example configuration for a user-positionable arm mechanism 400. The user-positionable arm mechanism 400 may include members 432, 434, and 438. The members 432 and 434 may be elongate members and may be longer than member 438.

As shown in FIGS. 3 and 4, the nut 370 may be attached to the member 432 at the first strut pivot joint 252, and the electromagnetic clutch 380 may be attached to the member 438 at the second strut pivot joint 254. The member 438 may be disposed at a distal end of the user-positionable arm mechanism 400. If the members 432 and 434 were pivotably attached to a supporting tower (such as, for example, the tower 104 shown in FIG. 1) at locations 433 and 435, respectively, then the user-positionable arm mechanism 400 would form a four member linkage.

In some implementations, each of the members 432, 434 may have a length L. In some instances, the length L may be in the range of 15 inches to 30 inches. In other instances, the length L may be larger than 30 inches or smaller than 15 inches. The length L may be any desired length.

In some implementations, rotation of the lead screw 360 (such as, for example, with application of electrical voltage to the electromagnetic clutch 380) may provide 15 inches to 30 inches of vertical travel of a microscope head (such as, for example, microscope head 120 show in FIG. 1) mounted to the member 438. Once again, though, the scope of the disclosure is not so limited. Rather, the vertical travel of a microscope head (or any other device attached to member 438) may be any desired amount of vertical travel.

Figure 5:
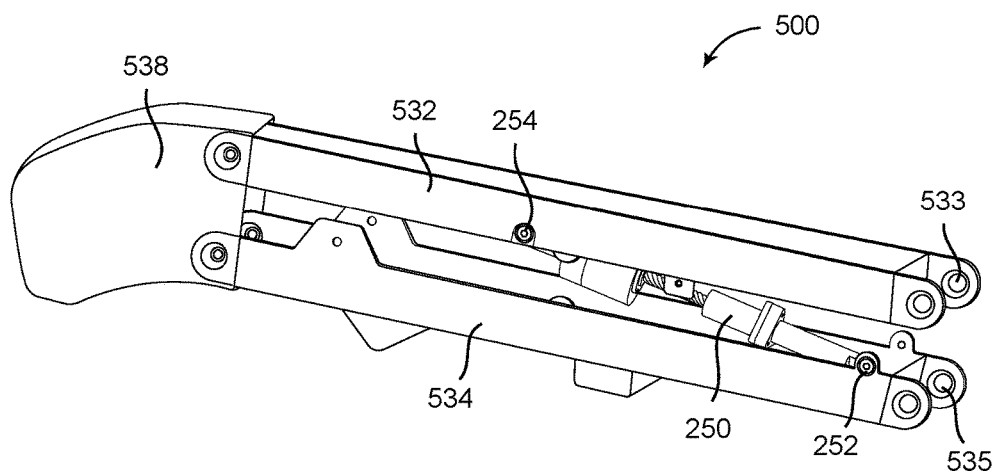
FIG. 5 depicts an example user-positionable arm mechanism for an ophthalmic surgical apparatus.

FIG. 5 depicts another example configuration for a user-positionable arm mechanism 500. The user-positionable arm mechanism 500 may include members 532, 534, and 538. Members 532 and 534 may be elongate members and may be longer than member 538. The member 538 may be disposed at a distal end of the user-positionable arm mechanism 500.

Referring to FIGS. 3 and 5, the electromagnetic clutch 380 may be attached to a member 532 at the second strut pivot joint 254, and the nut 370 may be attached to the member 534 at the first strut pivot joint 252. The members 532 and 534 are shown to be pivotably attached to the member 538. If the members 532 and 534 were also pivotably attached to a supporting tower (such as, for example, the tower 104 shown in FIG. 1) at locations 533 and 535, respectively, then the user-positionable arm mechanism 500 would form a four member linkage.

Figure 6:
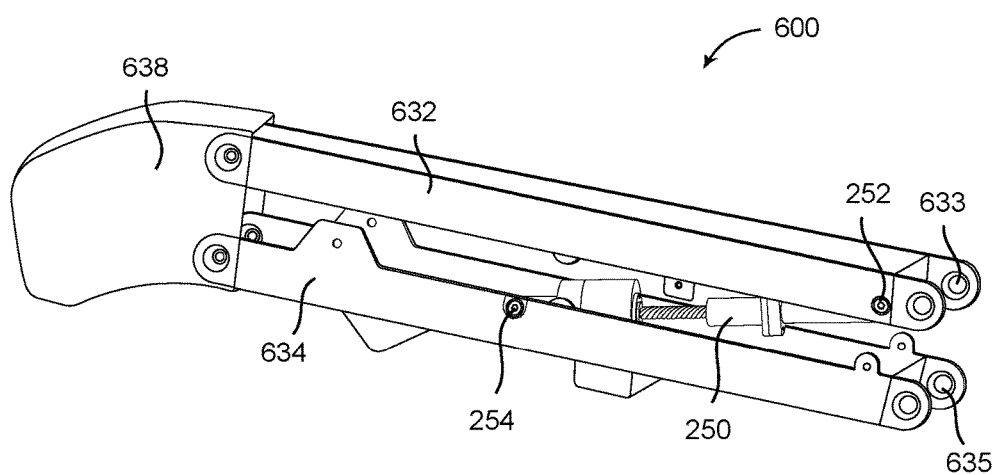
FIG. 6 depicts an example user-positionable arm mechanism for an ophthalmic surgical apparatus.

FIG. 6 depicts another example configuration for a user-positionable arm mechanism 600. The user-positionable arm mechanism 600 may include members 632, 634, and 638. Members 632 and 634 may be elongate members and may be longer than member 638. The member 638 may be disposed at a distal end of the user-positionable arm mechanism 600.

Referring to FIGS. 3 and 6, the nut 370 may be attached to the member 632 at the first strut pivot joint 252, and the electromagnetic clutch 380 may be attached to the member 634 at the second strut pivot joint 254. The members 632 634 are shown to be pivotably attached to the member 638. If the members 632 634 were also pivotably attached to a supporting tower (such as, for example, the tower 104 shown in FIG. 1) at locations 633 and 635, respectively, then the user-positionable arm mechanism 600 would form a four member linkage.

In the foregoing disclosure, the various implementations are described with reference to specific example implementations, but those skilled in the art will recognize that the scope of the disclosure is not limited to those. One or more of these example implementations may provide an ophthalmic surgical device (such as an ophthalmic microscope) with a user-positionable arm having improved reliability, reduced backlash, or smoother or quieter operation. It is fully contemplated that the features, components, and/or steps described with respect to one implementation may be combined with the features, components, and/or steps described with respect to other implementations of the present disclosure.

It is contemplated that various features and aspects of the various implementations may be used individually or jointly and possibly in a different environment or application. The disclosure and drawings are, accordingly, to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

What is claimed is:

1. An ophthalmic microscope comprising:
   a support base;
   a tower extending upward from the support base;
   a user-positionable arm extending from the tower and having a supported end that is attached to the tower; and
   a microscope head attached to a distal end of the user-positionable arm, the user-positionable arm comprising:
      a four component linkage comprising four components that are pivotably connected to each other;
      an electromagnetic brake strut pivotably attached in a diagonal relationship to at least two of the four components at a first strut pivot joint and at a second strut pivot joint, the electromagnetic brake strut comprising:
         a rotatable lead screw comprising:
            a first lead screw end region; and
            a second lead screw end region;
         a nut attached to the first strut pivot joint, the first lead screw end region received into the nut; and
         an electromagnetic clutch attached to the second strut pivot joint, the electromagnetic clutch operable to permit rotation of the rotatable lead screw relative to the electromagnetic clutch when an electrical voltage is applied to the electromagnetic clutch,
         wherein the electromagnetic clutch comprises:
            a rotor coupled to the lead screw such that the rotor and the lead screw rotate together;
            a friction plate slideably received into the rotor;
            a brake housing comprising a friction engaging surface configured to engage a surface of the friction plate; and
            a spring disposed between the rotor and the friction plate, the spring configured to bias the friction plate towards the brake housing.

2. The ophthalmic microscope of claim 1, wherein a first component and a second component of the four member linkage are longer than a third component and a fourth component of the four component linkage, wherein the first component and second component are pivotably connected by the third component and the fourth component, the first component being positioned offset from the second component, the third component attached to the tower, and the fourth component attached to the microscope head.

3. The ophthalmic microscope of claim 2, wherein the four component linkage forms a parallelogram shape with the first component and the second component being parallel to each other.

4. The ophthalmic microscope of claim 2, wherein the electromagnetic brake strut has a backdriving configuration.

5. The ophthalmic microscope of claim 2, wherein the nut is attached to the second component at the first strut pivot joint, and the electromagnetic clutch is attached to the fourth component at the second strut pivot joint.

6. The ophthalmic microscope of claim 2, further comprising a weight compensation strut pivotably attached to the first component and the second component, the weight compensation strut comprising a compressed gas spring.

7. The ophthalmic microscope of claim 6, wherein the weight compensation strut has a compressed length in the range of 254 mm (10 inches) to 762 mm (30 inches), and forms an angle with the first component, the angle being in the range of 5 degrees to 15 degrees.

8. The ophthalmic microscope of claim 2, wherein each of the first component and the second component defines an arm length in the range of 381 mm (15 inches) to 762 mm (30 inches), and wherein rotation of the rotatable lead screw provides 381 mm (15 inches) to 762 mm (30 inches) of vertical travel of the microscope head.

9. The ophthalmic microscope of claim 1, wherein the tower defines a vertical axis, and wherein the supported end of the user-positionable arm is rotatably attached to the tower to allow rotation of the user-positionable arm relative to the tower about the vertical axis.

10. The ophthalmic microscope of claim 1, further comprising a display screen that is electrically coupled to the microscope head.

11. The ophthalmic microscope of claim 1, wherein the rotatable lead screw comprises stainless steel and includes external threads having a spiral lead in the range of 12.7 mm (0.5 inches) per turn to 50.8 mm (2 inches) per turn, and wherein the nut has an internally threaded bore that is engaged with external threads of the rotatable lead screw.

12. The ophthalmic microscope of claim 1, wherein the rotatable lead screw comprises an external spiral bearing race, and wherein the nut comprises a plurality of internal metal balls that roll partially within the external spiral bearing race.

13. The ophthalmic microscope of claim 1, wherein the electromagnetic clutch comprises a bearing that supports the second lead screw end region.

14. The ophthalmic microscope of claim 1, wherein the brake housing further comprises:

a magnet operable to produce a first magnetic force that attracts the friction plate; and
an electromagnet operable to produce a second magnetic force that exceeds the first magnetic force that repels the friction plate from the brake housing when the electromagnet is energized.

15. An ophthalmic surgical apparatus comprising:
a rolling base;
a tower extending from the rolling base;
a user-positionable arm extending from the tower and having a supported end that is attached to the tower; and
an optical instrument attached to a distal end of the user-positionable arm, the user-positionable arm comprising:
  a four component linkage having four components that are pivotably connected to each other;
  an electromagnetic brake strut pivotally attached in a diagonal relationship to at least two of the four components at a first strut pivot joint and a second strut pivot joint, the electromagnetic brake strut comprising:
    a rotatable lead screw having a first screw end region and a second lead screw end region;
    a nut attached to the first strut pivot joint, the first lead screw end region threaded into the nut; and
    an electromagnetic clutch that allows lead screw rotation when an electrical voltage is applied thereto, the electromagnetic clutch attached to the second strut pivot joint,
  wherein the electromagnetic clutch comprises:
    a rotor coupled to the lead screw such that the rotor and the lead screw rotate together;
    a friction plate slideably received into the rotor;
    a brake housing comprising a friction engaging surface configured to engage a surface of the friction plate; and
    a spring disposed between the rotor and the friction plate, the spring configured to bias the friction plate towards the brake housing.

16. The ophthalmic surgical apparatus of claim 15, wherein the four components comprise:
a first component;
a second component;
a third component; and
a fourth component, wherein and the first component and the second component are pivotably connected by the third component and the fourth component, wherein the first component is positioned above the second component, wherein the third component is attached to the tower, and wherein the fourth component is attached to the optical instrument.

17. The ophthalmic surgical apparatus of claim 16, wherein the four component linkage forms a parallelogram shape with the first component and the second component being parallel to each other.

18. The ophthalmic surgical apparatus of claim 16, wherein the nut is attached to the second component at the first strut pivot joint, and wherein the electromagnetic clutch is attached to the fourth component at the second strut pivot joint.

19. The ophthalmic surgical apparatus of claim 16, further comprising a weight compensation strut pivotably attached to the first component and the second component, the weight compensation strut comprising a compressed gas spring.

20. The ophthalmic surgical apparatus of claim 15, wherein the tower defines a vertical axis, and wherein the supported end of the user-positionable arm is rotatably attached to the tower to allow rotation of the user-positionable arm relative to the tower about the vertical axis.

21. The ophthalmic surgical apparatus of claim 15, wherein the electromagnetic brake strut has a backdriving configuration.

22. The ophthalmic surgical apparatus of claim 15, wherein the brake housing further comprises:
a magnet operable to produce a first magnetic force that attracts friction plate; and
an electromagnet operable to produce a second magnetic force that exceeds the first magnetic force that repels the friction plate from the brake housing when the electromagnet is energized.

* * * * *